(12) United States Patent
Keller

(10) Patent No.: US 6,984,249 B2
(45) Date of Patent: Jan. 10, 2006

(54) KNEE PROSTHESIS WITH A FLEXION HINGE

(75) Inventor: Arnold Keller, Kayhude (DE)

(73) Assignee: Walde mar Link GmbH & Co. KG, Hamburg (DE)

( * ) Notice: Subject to any disclaimer, the term of this patent is extended or adjusted under 35 U.S.C. 154(b) by 0 days.

(21) Appl. No.: 10/474,954

(22) PCT Filed: Apr. 15, 2002

(86) PCT No.: PCT/EP02/04156

§ 371 (c)(1),
(2), (4) Date: May 6, 2004

(87) PCT Pub. No.: WO02/085257

PCT Pub. Date: Oct. 31, 2002

(65) Prior Publication Data
US 2004/0186584 A1 Sep. 23, 2004

(30) Foreign Application Priority Data
Apr. 25, 2001 (EP) .................................. 01110261

(51) Int. Cl.
A61F 2/38 (2006.01)
(52) U.S. Cl. .................. 623/20.24; 623/20.29
(58) Field of Classification Search ............. 623/20.24, 623/20.25, 20.28, 20.29, 20.31, 20.12, 20.14, 623/20.26, 20.27
See application file for complete search history.

(56) References Cited

U.S. PATENT DOCUMENTS

| 3,696,446 A | * | 10/1972 | Bousquet et al. ........ 623/20.26 |
| 3,772,709 A | | 11/1973 | Swanson |
| 3,845,525 A | | 11/1974 | Gaylord |
| 3,885,252 A | * | 5/1975 | Nakajima ................. 623/20.24 |
| 4,134,158 A | * | 1/1979 | Laure ....................... 623/20.24 |
| 5,411,555 A | * | 5/1995 | Nieder ..................... 623/20.26 |
| 2005/0107886 A1 | * | 5/2005 | Crabtree et al. ......... 623/20.24 |

FOREIGN PATENT DOCUMENTS

| DE | 3119622 A1 | 11/1982 |
| DE | 31 19 841 C2 | 12/1982 |
| DE | 3730175 C1 * | 9/1988 |
| EP | 0 278 184 A1 | 8/1988 |
| EP | 0 420 460 A1 | 4/1991 |

(Continued)

OTHER PUBLICATIONS

English Translation of International Preliminary Examination Report for PCT/EP02/04156 dated Jun. 23, 2003.

*Primary Examiner*—Paul B. Prebilic
(74) *Attorney, Agent, or Firm*—Morrison & Foerster LLP

(57) ABSTRACT

A knee prosthesis with a flexion hinge which is formed by a hinge fork with two branches lying opposite each other, by a center part which is to be fitted in the hinge fork transversely with respect to the flexion axis of the latter, and by a hinge pin which, after the center part has been fitted into the hinge fork, is to be mounted, by movement in its longitudinal direction, in aligned hinge bores of the hinge fork and of the center part. So as not to have to push the pin into the prosthesis from the outside, it is formed by two pin stumps which, in an assembly position, are arranged inside the center part and, in a mounted position, partially protrude from the latter.

13 Claims, 2 Drawing Sheets

FOREIGN PATENT DOCUMENTS

| | | |
|---|---|---|
| EP | 0 716 039 A1 | 6/1996 |
| EP | 0 791 343 A2 | 8/1997 |
| FR | 2.161.588 | 7/1973 |
| GB | 1 305 391 | 1/1973 |
| JP | 01221157 * | 9/1989 |
| JP | 06105855 * | 4/1994 |

* cited by examiner

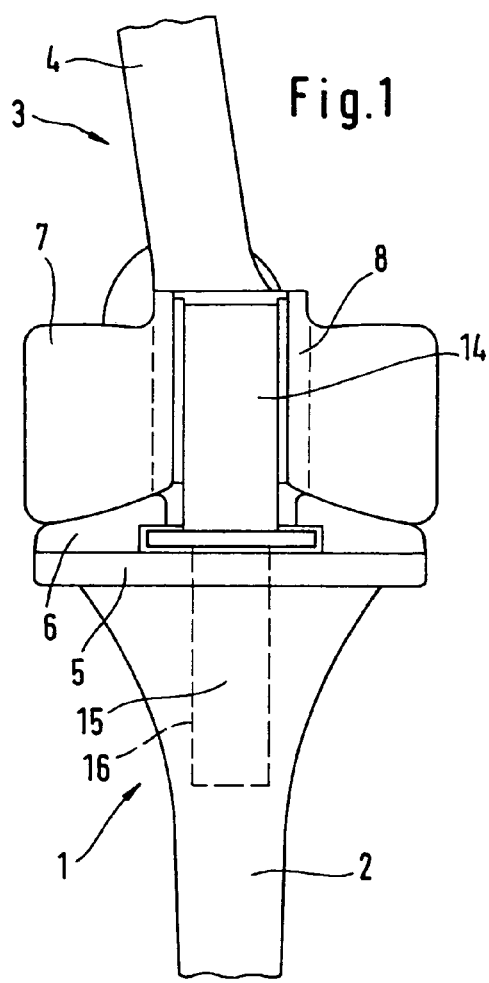
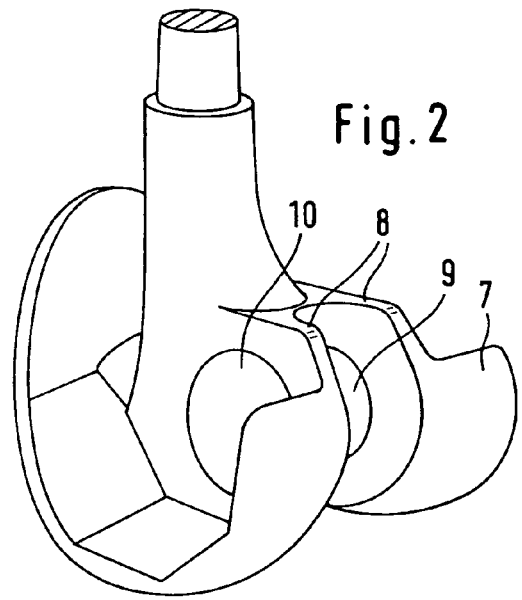
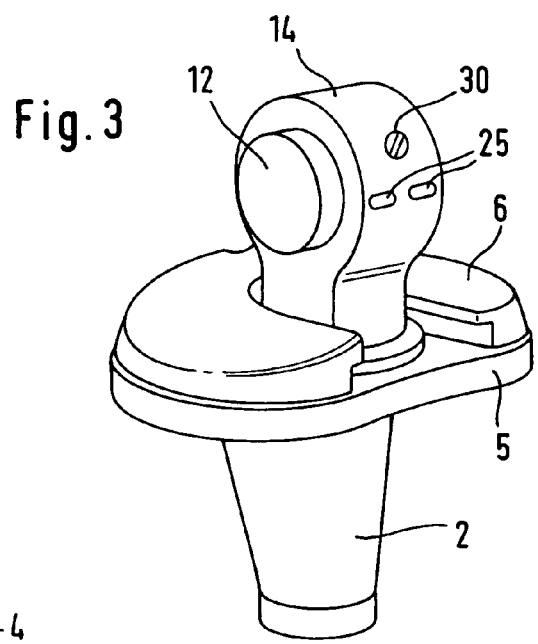
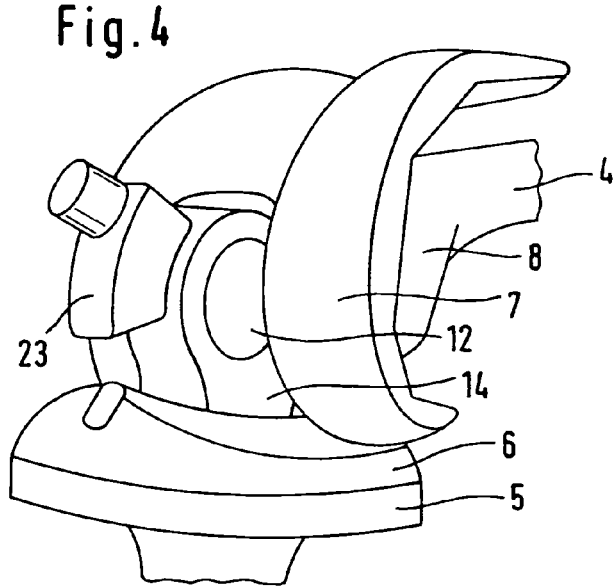
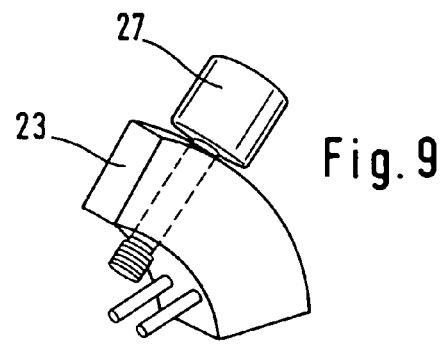

KNEE PROSTHESIS WITH A FLEXION HINGE

FIELD AND BACKGROUND OF THE INVENTION

The invention relates to knee prostheses which have a hinge for determining the flexion movement. This can be a hinge which is used exclusively for stabilization (DE-C-31 19 841, EP-A-716 839, EP-A-791 343, EP-A-420 460) or which transmits the full load (GB-C-1 305 391, EP-A-278184, FR-C-2 161 588, U.S. Pat. No. 3,772,709). The hinge is in each case formed by a hinge fork which is normally connected to the femur, and by a hinge centre piece which is connected to the tibia. The branches of the hinge fork and the centre piece have aligned bores through which a hinge pin passes. Generally, the femoral and tibial components of the prosthesis are first implanted separately and then connected to one another. In those cases where only the hinge pin connects the components to one another, it is pushed into the associated receiving bores from the side after the components have been implanted. This makes necessary a corresponding insertion opening in one of the femoral condyles, which adversely weakens the bone and involves additional work during the operation. In those prostheses which contain the hinge in a stabilizing part which is connected to the tibial component via a rotation bearing having a journal parallel to the tibia, the components are most often joined together by means of the journal which belongs to one component being inserted into the receiving bore of the other component. This has the disadvantage that the ligament apparatus of the knee has to be stretched considerably.

SUMMARY OF THE INVENTION

The invention avoids these disadvantages by use of two pin stumps which can adopt two positions instead of a single hinge pin. In a position used for assembly, they are held almost entirely within the hinge center part. They are recessed into this center part to such an extent that the latter can be fitted into the hinge fork from the side. Thereafter, the pin stumps are pushed out from the center part into the position which they assume in the mounted state and in which they protrude far enough into receiving bores provided in the fork branches.

The pin stumps do not require a long support length in the centre part of the hinge because the distance between the end faces of the centre part and the fork branches is very small, and the torque to be taken up by the pin stumps is also correspondingly small. However, it can be expedient for the pin stumps to have support projections which bear on the wall of the hinge bore of the centre part and/or on the respective other pin stump. The pin stumps with the projections have a length which is greater than half the length of the hinge bore in the centre apart and therefore are able to safely transmit the torques which arise. In a preferred embodiment, the support projection of one pin stump is formed by a journal which is guided in the support projection, designed as a cylinder, of the other pin stump. However, other support configurations are also conceivable. For example, each pin stump can have a ring of projections spaced apart like cogs around its circumference, which projections, in the assembly position, extend almost the entire length of the bore of the centre part between the projections of the other pin stump, set in the opposite direction, and in each case bear on the circumference of the receiving bore of the centre part.

To simplify the assembly, the pin stumps can be subject to the spreading force of a spring which moves them apart into the mounted position as soon as they are able to do so on reaching the receiving bores in the fork branches. For example, at the start of assembly, the centre part of the hinge is held between thumb and index finger in such a way that the pin stumps are pressed into the centre part. The latter is then pushed into the space between the fork branches so that the pin stumps are now held back in the centre part by bearing on the end face of the fork branches. It is only when the receiving bores are reached that the pin stumps snap apart into the mounted state under the effect of the spreader spring.

However, so that the operating surgeon does not have to focus his attention on securely holding the pin stumps at the start of assembly, it is possible for a retaining device to be provided.

This retaining device is intended to leave free at least part of the end face of the pin stump for insertion into the hinge fork, so that the retaining device can be released as soon as the centre part of the hinge is fitted with the pin stumps at least partially into the hinge fork.

For disassembly, it is necessary to draw the pin stumps back out of the receiving bores in the hinge fork. For this purpose, an opening is provided in the circumferential surface of the middle part at a position accessible during the operation, through which opening an instrument can gain access to suitable grip surfaces on the pin stumps. This opening can be an oblong hole, or two oblong holes assigned one to each pin stump. The instrument can also be used to assist the spreading manoeuvre if the spring force is insufficient or if the physician wishes to ensure that the pin stumps have reached their final mounted position.

It is not necessary to secure the pin stumps in the mounted position since there is no reason to be concerned about forces by which they could be drawn back into the assembly position. If one wishes to make sure, however, such a safety device may be provided.

BRIEF DESCRIPTION OF THE DRAWINGS

The invention is explained in greater detail below with reference to the drawing which represents an advantageous illustrative embodiment and in which:

FIG. 1 shows a dorsal view of the principal parts of the prosthesis in the extended state, FIG. 2 shows a view of the femoral component obliquely from the side, FIG. 3 shows a view of the tibial component obliquely from the side, FIG. 4 shows a view of these parts during assembly, obliquely from the side, FIG. 9 shows a perspective view of the retaining device.

DETAILED DESCRIPTION OF THE INVENTION

Figure 5:
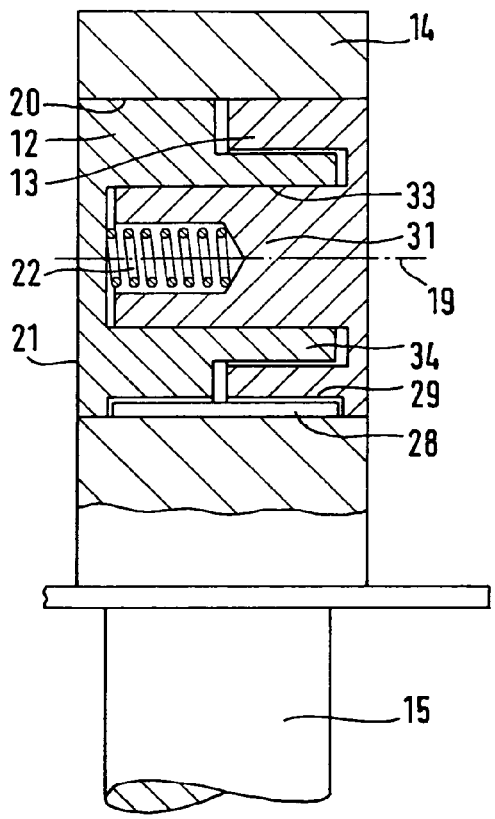
FIG. 5 shows a cross section through the centre part of the hinge, with the pin stumps in the assembly position.

The prosthesis consists of a tibial component 1 whose stem 2 is to be implanted in the tibia, and of a femoral component 3 whose stem 4 is to be implanted in the femur. At the top, the tibial component 1 ends in a plate 5 which carries a polyethylene plateau 6 whose top forms a slide surface for the runners 7 of the femoral component. The vertical load is transmitted via these parts.

To stabilize the components 1 and 3, a stabilizing arrangement is provided forming a hinge, which permits a flexion movement between the components 1 and 3, and a rotation bearing. The femoral component 3, with the plates 8 arranged parallel to one another in a box shape, forms a hinge fork with receiving bores 9 which are lined by hat-shaped polyethylene bearing parts 10 which form a hollow cylindrical bearing face 11. Mounted therein are pin parts 12, 13 whose other ends are arranged in the hinge centre part 14 which is arranged integrally on the upper end of a journal 15 which is mounted so as to rotate in a receiving bore 16 which is provided approximately parallel to the stem 2 in the tibial component 1. This stabilizing arrangement ensures that the relative movement between the femoral component and the tibial component can take place exclusively as a flexion movement about the axis 19 of the pin stumps 12 or as a rotational movement about the axis of rotation defined by the bore 16.

The hinge centre part 14 sits virtually free of play between the branches 8 of the hinge fork, the rims 17 of the polyethylene parts 10 avoiding undesired metal-on-metal contact.

Figure 7:
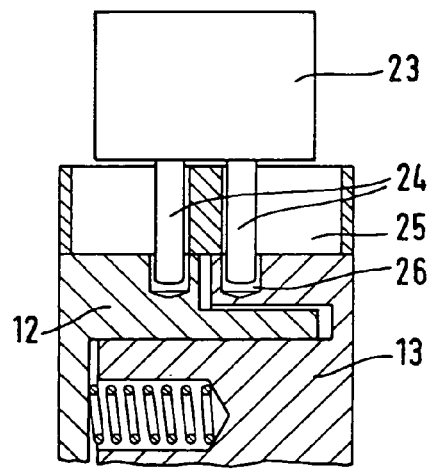
FIG. 7 shows a partial view of the centre part with the pin stumps held in the assembly position by means of a retaining device.

As FIG. 5 shows, the pin stumps 12, 13 can be drawn back or pressed into the bore 20 of the centre part 14 of the hinge in order to assume the assembly position. Their end faces 21 are then approximately flush with the end faces of the hinge centre part 14 and together are in any case not wider than the intermediate space available for assembly between the fork branches 8. At the circumference the axial dimension of each pin stump 12, 13 is approximately half as much as the corresponding dimension of the hinge centre part 14. By means of a compression spring 22, they are forced out of this assembly position into the position to be assumed in the mounted state. To ensure that this does not happen too soon, they are held securely in the assembly position by a retaining device 23, as is shown in FIG. 7. This retaining device, which is shown separately in FIG. 9, has two rods 24 which are arranged at a defined and unchangeable distance and which engage via oblong holes 25 in the hinge centre part 14 into bores 26 of the pin stumps 12, 13. The retaining device 23 can be secured temporarily in this secured position by means of a screw 27 on the hinge centre part 14.

Figure 6:
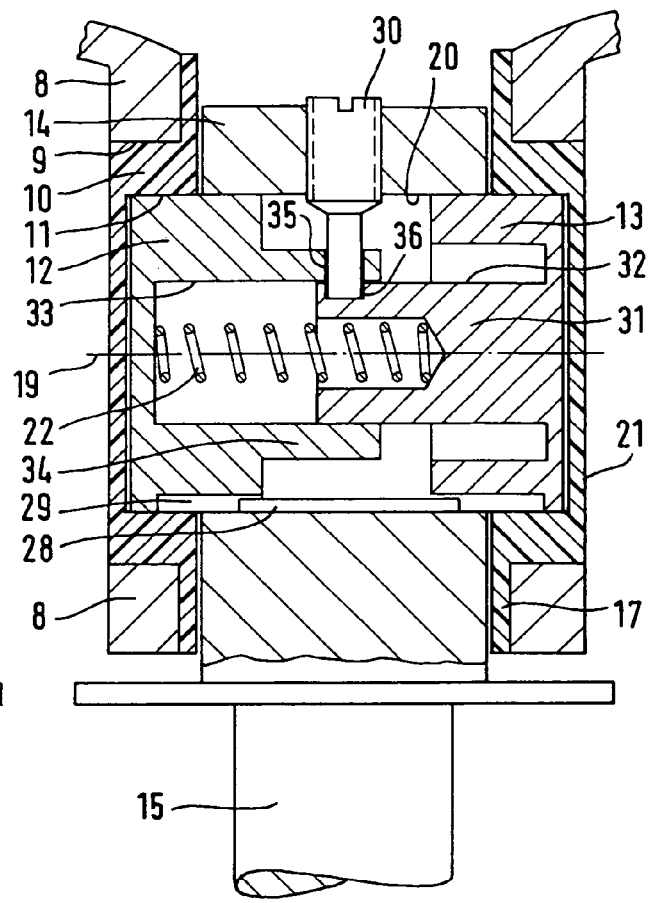
FIG. 6 shows a cross section through the hinge, with the pin stumps in the mounted position.
Figure 8:
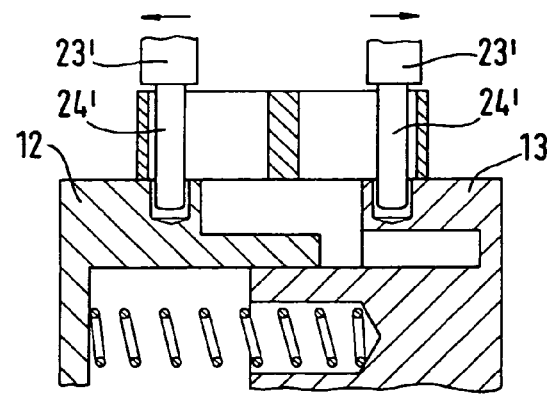
FIG. 8 shows a position corresponding to FIG. 7, with the pin stumps spread apart by an instrument.

As long as the stabilizing arrangement is situated in this assembly state, the tibial component 1 and the femoral component 3 can be joined together, as is shown in FIG. 4. As soon as the hinge centre part 14 is situated with the pin stumps 12, 13 between the fork parts 8, the retaining device 23 can be released and removed. As soon as the components have reached the relative position in which the bores in the fork branches 8 and in the hinge centre part 14 are flush with one another, the pin stumps 12, 13 snap apart under the effect of the spring 22 and into the receiving bores 11. By means of an instrument 23', of which only the rods 24' are shown in FIG. 8, the pin stumps 12, 13 can be spread farther if they have not already reached their end position under the effect of the spring 22. The physician can then secure the pin stumps 12, 13 in the mounted position by means of a screw 30 which, in the manner shown in FIG. 6, are provided in bores 35, 36 of support projections 31, 34 which are provided on the pin stumps 12, 13.

To ensure that the bores 26 can always be reached through the oblong holes 25 and do not disappear as a result of turning of the pin stumps 12, 13, an anti-rotation means is provided, namely a longitudinal rib 28 which is arranged in the bore 20 and cooperates with corresponding grooves 29 of the pin stumps 12, 13.

If the hinge centre part is made narrow, as is desired, the pin stumps 12, 13 cooperate with the bore 20, accommodating them, of the hinge centre part 14 only over a relatively small axial length. Although they are subjected to torques only slightly, if at all, it would appear to be expedient to provide an additional form of support. In the example shown, this is achieved by the fact that the pin stump 13 has a support journal 31 whose cylindrical circumferential surface 32 is guided tightly in a cylindrical bore 33 of a support projection 34 of the pin stump 12. In the mounted state, these surfaces also remain in a state in which they support and guide each other.

If one wishes to remove the prosthesis components from one another, the pin stumps 12, 13 are drawn back together using the instrument indicated in FIG. 8. The hinge centre part can then be released from the hinge fork 8.

What is claimed is:

1. A knee prosthesis comprising a flexion hinge which comprises a hinge fork with two branches lying opposite each other, a center part which is configured to be fitted into the hinge fork transversely with respect to a flexion axis of the hinge fork and a hinge pin which, after the center part has been fitted into the hinge fork, is configured to be mounted, by movement in its longitudinal direction, in aligned hinge bores of the hinge fork and of the center part, the hinge pin comprising two separate pin stumps which are inside the center part when the prosthesis is in a pre-assembly position and which are configured so as to partially protrude from the center part and extend into the hinge bores of the hinge fork when the prosthesis is in a mounted position.

2. The knee prosthesis according to claim 1, wherein the pin stumps comprise support projections which bear on a wall of the hinge bore of the center part and extend out over half the length of the hinge bore of the center part.

3. The knee prosthesis according to claim 2, wherein the support projection of one pin stump is formed by a journal which is guided in the support projection, designed as a cylinder, of the other pin stump.

4. The knee prosthesis according to claim 1, 2 or 3, further comprising a spring applying a spreading force to the pin stumps.

5. The knee prosthesis according to claim 4, further comprising a retaining device configured to hold the pin stumps in the pre-assembly position so as to leave free at least part of the end face of the pin stump for insertion between the fork branches.

6. The knee prosthesis according to claim 5, wherein the pin stumps are configured so as to be accessible by an instrument for spreading or drawing them back together, which instrument is introduced through an opening in the circumferential surface of the center part.

7. The knee prosthesis according to claim 1, 2 or 3, further comprising means for securing the pin stumps in the mounted position.

8. A knee prosthesis comprising a flexion hinge which comprises a hinge fork with two branches lying opposite each other, a center part which is configured to be fitted into the hinge fork transversely with respect to a flexion axis of the hinge fork and a hinge pin which, after the center part has been fitted into the hinge fork, is configured to be mounted, by movement in its longitudinal direction, in aligned hinge bores of the hinge fork and of the center part, the hinge pin comprising two separate pin stumps which are inside the center part when the prosthesis is in a pre-assembly position and which are configured so as to partially protrude from the center part when the prosthesis is in a mounted position, the pin stumps comprising support projections which bear on a wall of the hinge bore of the center part and extend out over half the length of the hinge bore of the center part.

9. The knee prosthesis according to claim 8, wherein the support projection of one pin stump is formed by a journal which is guided in the support projection, designed as a cylinder, of the other pin stump.

10. The knee prosthesis according to claim 8 or 9, further comprising a spring applying a spreading force to the pin stumps.

11. The knee prosthesis according to claim 10, further comprising a retaining device configured to hold the pin stumps in the pre-assembly position so as to leave free at least part of the end face of the pin stump for insertion between the fork branches.

12. The knee prosthesis according to claim 11, wherein the pin stumps are configured so as to be accessible by an instrument for spreading or drawing them back together, which instrument is introduced through an opening in the circumferential surface of the center part.

13. The knee prosthesis according to claim 8 or 9, further comprising means for securing the pin stumps in the mounted position.

* * * * *

UNITED STATES PATENT AND TRADEMARK OFFICE
CERTIFICATE OF CORRECTION

PATENT NO.        : 6,984,249 B2                                    Page 1 of 1
APPLICATION NO.   : 10/474954
DATED             : January 10, 2006
INVENTOR(S)       : Arnold Keller It is certified that error appears in the above-identified patent and that said Letters Patent is hereby corrected as shown below:

On the title Page, item (73), Under Assignee:

Delete the space in "Walde mar" and replace with --Waldemar--

Signed and Sealed this

Twenty-ninth Day of May, 2007

JON W. DUDAS
*Director of the United States Patent and Trademark Office*